US006486214B1

(12) United States Patent
Uhrich

(10) Patent No.: US 6,486,214 B1
(45) Date of Patent: Nov. 26, 2002

(54) POLYANHYDRIDE LINKERS FOR PRODUCTION OF DRUG POLYMERS AND DRUG POLYMER COMPOSITIONS PRODUCED THEREBY

(75) Inventor: Kathryn E. Uhrich, Hoboken, NJ (US)

(73) Assignee: Rutgers, The State University of New Jersey, New Burnswick, NJ (US)

( * ) Notice: Subject to any disclaimer, the term of this patent is extended or adjusted under 35 U.S.C. 154(b) by 0 days.

(21) Appl. No.: 09/627,215

(22) Filed: Jul. 27, 2000

Related U.S. Application Data

(63) Continuation-in-part of application No. 09/422,294, filed on Oct. 21, 1999, which is a continuation-in-part of application No. PCT/US98/18816, filed on Sep. 10, 1998
(60) Provisional application No. 60/058,328, filed on Sep. 10, 1997.

(51) Int. Cl.$^7$ ...................... A61K 47/32; A61K 31/195; A61K 31/43; A61K 31/545
(52) U.S. Cl. .................... 514/772.5; 514/197; 514/201; 514/567
(58) Field of Search ............................. 514/772.5, 197, 514/201, 567

(56) References Cited

U.S. PATENT DOCUMENTS

| | | | |
|---|---|---|---|
| 4,062,855 A | 12/1977 | Allan et al. | 260/295 PA |
| 4,126,445 A | 11/1978 | Allan et al. | 71/94 |
| 4,684,620 A | 8/1987 | Hruby et al. | 514/11 |
| 4,757,128 A | 7/1988 | Domb et al. | 528/271 |
| 4,792,598 A | 12/1988 | Ziegast | 528/206 |
| 4,857,311 A | 8/1989 | Domb et al. | 424/78 |
| 4,868,274 A | 9/1989 | Gupta et al. | 528/206 |
| 4,886,870 A | 12/1989 | D'Amore et al. | 528/206 |
| 4,888,176 A * | 12/1989 | Langer et al. | 424/426 |
| 4,891,225 A | 1/1990 | Langer et al. | 424/428 |
| 4,906,474 A | 3/1990 | Langer et al. | 424/428 |
| 4,997,904 A | 3/1991 | Domb | 528/206 |
| 4,999,417 A | 3/1991 | Domb | 528/271 |
| 5,082,925 A | 1/1992 | Shalaby et al. | 528/354 |
| 5,175,235 A | 12/1992 | Domb et al. | 528/271 |
| 5,259,968 A | 11/1993 | Emert et al. | 252/51.5 A |
| 5,264,540 A | 11/1993 | Cooper et al. | 528/272 |
| 5,498,729 A | 3/1996 | Domb | 548/500 |
| 5,514,764 A | 5/1996 | Fretchet et al. | 528/10 |
| 5,545,409 A | 8/1996 | Laurencin et al. | 424/426 |
| 5,629,009 A | 5/1997 | Laurencin et al. | 424/426 |
| 5,902,599 A | 5/1999 | Anseth et al. | 424/426 |
| 5,942,252 A | 8/1999 | Tice et al. | 424/501 |
| 6,071,530 A | 6/2000 | Polson et al. | 424/426 |

FOREIGN PATENT DOCUMENTS

| | | | |
|---|---|---|---|
| DE | 288311 | 3/1991 | A01N/25/10 |
| DE | 288387 | 3/1991 | C08G/67/04 |
| EP | 0246341 | 11/1987 | A61L/27/00 |
| WO | 91/09831 | 7/1991 | C07C/69/035 |
| WO | 97/39738 | 10/1997 | A61K/9/16 |
| WO | 98/36013 | 8/1998 | C08G/64/00 |
| WO | 99/12990 | 3/1999 | C08G/63/00 |
| WO | 99/29885 | 6/1999 | C12P/1/00 |

OTHER PUBLICATIONS

Anastasiou, T.J., et al., "Novel Polyanhydrides with Enhanced Thermal and Solubility Properties", *Macromolecules, 33*(17), pp. 6217–6221, (2000).

Anastasiou, T.J., et al., "Novel Degradable Polyanhydrides", *25th Annual Meeting Transactions of the Society for Biomaterials*, p. 79, (1999).

Anastasiou, T.J., et al., "Synthesis of Novel, Degradable Polyanhydrides Containing Para–Aminosalicylic Acid as Drug Delivery Devices for Tuberculosis Treatment", *Polymer Preprints, 41*(2), pp. 1366–1367, (Aug. 2000).

Attawia, M.A., et al., "Bicompatibility Testing of Poly(anhydride–co–imides) Containing Pyromellitylimidoalanine", *The 21st Annual Meeting of the Society for Biomaterials*, Boston, Mass, p. 222, (1994).

Attawia, M.A., et al., "Cytototoxicity testinf of poly(anhydride–co–imides) for orthopedic applications", *Journal of Biomedical Materials Research, 29*, pp. 1233–1240, (1995).

Attawia, M.A., et al., "In Vitro Bone Biocompatibility of Poly(anhydride–co–imides) Containing Pyromellitylimidoalanine", *Journal of Orthopedic Research, 14*, pp. 445–454, (1996).

Attawia, M.A., et al., "Proliferation, Morphology, and Protein Expression by Osteoblasts Cultured on Poly(anhydride––co–imides)", *J. Biomed. Mater. Res. (Appl. Biomater.), 48*, pp. 322–327, (1999).

Attawia, M.A., et al., "The Long Term Osteoblast Response to Poly(anhydride–co–imides) : A New Degradable Polymer for Use in Bone", *Proceedings of the Fifth World Biomaterials Congress*, Toronto, Canada, p. 113, (1996).

Beaton, M.L., et al. "Synthesis of a novel poly(anhydride–ester)", *The Rutgers Scholar—An Electronic Bulletin of Undergraduate Research, 3*, www.rutgersscholar.rutgers.edu/volume03/beatuhri/beatuhri.html, 7 p., (2001).

Bedell, C., et al., "Processing and Hydrolytic Degradation of Aromatic, Ortho–Substituted Polyanhydrides", *Journal of Applied Polymer Science, 80*, pp. 32–38, (2001).

Campo, C.J., et al., "Polyanhydrides: the effects of ring substitution changes on polymer properties", *Polymer Bulletin, 42*, pp. 61–68, (1999).

Chafi, N., et al., "Dosage form with salicylic acid attached to a polyanhydride polymer dispersed in an Eudragit matrix", *International Journal of Pharmaceutics*, vol. 52, pp. 203–211, (1989).

(List continued on next page.)

*Primary Examiner*—Thurman K. Page
*Assistant Examiner*—Blessing Fubara
(74) *Attorney, Agent, or Firm*—Schwegman, Lundberg, Woessner & Kluth, P.A.

(57) ABSTRACT

Polyanhydrides which link low molecular weight drugs containing a carboxylic acid group and an amine, thiol, alcohol or phenol group within their structure into polymeric drug delivery systems are provided. Also provided are methods of producing polymeric drug delivery systems via these polyanhydride linkers as well as methods of administering low molecular weight drugs to a host via the polymeric drug delivery systems.

3 Claims, No Drawings

OTHER PUBLICATIONS

Conix, A., "Aromtaic Polyanhydrides, a New Class of High Melting Fiber–Forming Polymers", *Journal of Polymer Science, XXIX*, pp. 343–353, (1958).

Conix, A., "New High–Melting Fibre–Forming Polymers", *Die Makromolekulare Chemie, XXIV*, pp. 76–78, (1957).

Conix, A., "Poly[1,3–bis (p–carboxyphenoxy)–Propane anhydride]", *Macromolecular Synthesis*, 2, pp. 95–99, (1996).

Domb, A.J., "Synthesis and Characterization of Biodegradable Aromatic Anhydride Copolymers", *Macromolecules*, 25, pp. 12–17, (1992).

Dukovic, G., et al., "Novel degradable poly(anhydride–esters) for controlled drug release", *The Rutgers Scholar—An electronic Bulletin of Undergraduate Research*, 1, http://rutgersscholar.rutgers.edu/volume01/uhriduko/uhriduko.html, 10 p., (1999).

Erdmann, L., et al., "Degradable poly(anhydride ester) implants: effects of localized salicylic acid release on bone", *Biomaterials 21*, pp. 2507–2512, (2000).

Erdmann, L., et al., "Chapter 5: Polymeric Prodrugs: Novel Polymers with Bioactive Components", *In: Tailored Polymeric Materials for Controlled Delivery Systems*, I. McCulloch, et al., (Eds.) ACS Symposium Series 709, American Chemical Society: Washington, D.C., pp. 83–91, (1998).

Erdmann, L., et al., "Polymer Prodrugs with Pharmaceutically Active Degradation Products", *Polymer Preprints*, 38 (2), pp. 570–571, (Aug. 1997).

Erdmann, L., et al., "Polymeric Prodrugs: Novel Polymers for Delivery of Salicylic Acid", *Annals of Biomedical Engineering*, 26 (*Suppl. 1*), Abstract No. PB.26, Annual Fall Meeting, p. S–124, (1998).

Erdmann, L., et al., "Polymeric Salicylic Acid: In Vitro and In Vivo Degradation", *Polymer Preprints*, 39 (2), pp. 224–225, (Aug. 1998).

Erdmann, L., et al., "Synthesis and Characterization of a Polymeric Prodrug", *Proceedings of the American Chemical Society Division of Polymeric Materials: Science and Engineering*, 78, Abstract of Spring Meeting, Dallas, TX, pp. 194, (Apr. 1998).

Erdmann, L., et al., "Synthesis and degradation characteristics of salicylic acid–derived poly(anhydride–esters)", *Biomaterials*, 21, pp. 1941–1946, (2000).

Giammona, G., "Polymeric Prodrugs alpha beta poly–hydroxyethyl–dl–aspartamide as macromolecular carrier for some non steroidal anti–inflammatory agents", *Abstract from Database BIOSIS Online, Biosciences Information Service, Philadelphia, PA*, Original publication from International Journal of Pharmaceutics (Amsterdam), 1 p., (1989).

Gouin, S., et al., "New Polyanhydrides Made from a Bile Acid Dimer and Sebacic Acid: Synthesis, Characterization, and Degradation", *Macrmolecules*, 33, pp. 5379–5383, (2000).

Ibim, S., et al., "Controlled Release Based on Poly(anhydride–co–Imides)", *Proceed. Intern. Symp. Control. Rel. Bioact. Mater.*, 22, 2 pgs., (1995).

Ibim, S.E., et al., "Preliminary In Vivo Report on the Osteocompatibility of Poly(anhydride–co–imides) Evaluated in a Tibial Model", *Appp. Biomater.*, 43(4), pp. 374–379, (1998).

Ibim, S.M., et al., "Poly(anhydride–co–imides): In vivo biocompatibility in a rat model", *Biomaterials*, 19, pp. 941–951, (1998).

Krogh–Jespersen, E., et al., "Synthesis of a Novel Aromatic Polyanhydride Containing Aminosalicyclic Acid", *Polymer Preprints*, 41 (1), pp. 1048–1049, (Mar. 2000).

Langer, R., "New Methods of Drug Delivery", *Science*, 249, pp. 1527–1533, (Sep. 1990).

Laurencin, C.T., et al., "Poly(anhydrides–co–imides) : In Vivo Biocompatibility Study", *23rd Annual Meeting of the Society for Biomaterials*, New Oreleans, LA, p. 483, (1997).

Laurencin, C.T., et al., "The Biocompatibility of Poly(anhydride–co–imides) : High Strength Polymers for Controlled Drug Delivery", *Proc. 24th Int'l. Symp. Control. Rel. Bioact. Mater.*, pp. 973–974, (1997).

Laurencin, C.T., et al., "The Bone Biocompatibility of Poly(anhydride–co–imides)—A New Generation Degradable Polymer for Orthopedic Applications", *41st Annual Meeting of the Orthopedic Research Society*, Orlando, FL, p. 143–24, (1995).

Laurencin, C.T., et al., "The Controlled Delivery of Radiosensitizers: Taxol Treatment fro Ewing Sarcoma", *Proceedings of the 25th Int'l Symp. Control. Rel. Bioact. Mater.*, pp. 236–237, (1998).

Macedo, B., et al., "The in vivo Response to a Bioactive Biodegadable Polymer", *Journal of Dental Research*, 78, Abstract No. 2827, p. 459, (1999).

Macedo, B., et al., "The in vivo response to bioactive polanhydride monofilament", *Journal of Dental Research*, 79, Abstract No. 3872, p. 627, (2000).

Pinther, P., et al., "Synthesis of polyanhydrides containing ester groups", *Die Makromolekulare Chemie, Rapid Communications*, 11, pp. 403–408, (Aug. 11, 1990).

Seidel, J.O., et al., "Erosion of Poly(anhydride–co–imides): A Preliminary Mechanistic Study", *J. Appl. Polym. Sci.*, 62(8), pp. 1277–1283, (1996).

Shen, E., et al., "Morphological Characterization of Erodible Polymer Carriers for Drug Release", *Proc. 26th Int'l Symp. Control. Rel. Bioact. Mater.*, pp. 717–718, (1999).

Uhrich, K.E., et al., "Chemical Changes during in vivo degradation of poly(anhydride–imide) matrices", *Biomaterials*, 19, pp. 2045–2050, (1998).

Uhrich, K.E., et al., "Degradation of poly(anhydride–co–imides) : Novel Polymers for Orthopedic Applications", *Mat. Res. Soc. Symp. Proc.*, 394, pp. 41–46 (1995).

Uhrich, K.E., et al., "In Vitro Degradation Characteristics of Poly(anhydride–imides) Containing trimellitylimidoglycine", *J. Appl. Polymer Sci.*, 63 (11), pp. 1401–1411, (1997).

Uhrich, K.E., et al., "In Vitro Degradation Characteristics of Poly(anhydride–imides) Containing Pyromellitylimidoalanine", *J. Appl. Polym. Sci., Part A, Polym. Chem.*, 34 (7), pp. 1261–1269, (1996).

Uhrich, K.E., et al., "Poly(anhydride–ester) Degradation: Mechanical Changes and Correlation to Antibiotic Release", *American Chemical Society, Abstracts of Papers, Part 2, Abstract No. 121,* 2221st ACS National Meeting, San Diego, CA, 1 p., (Apr. 2001).

Uhrich, K.E., et al., "Synthesis and Characterization of Degradable Poly(anhydride–co–imides)", *Macromolecules, 28* (7), pp. 2184–2193, (1995).

Uhrich, K.E., et al., "Synthesis and Characterization of poly(anhydride–co–imides): Solution Polycondensation of Biodegradable Polymers Derived from Amino Acids", *Proceedings of the American Chemical Society Division of Polymeric Materials: Science and Engineering, 70,* Spring Meeting, San Diego, CA, pp. 239–240, (1994).

Uhrich, K.E., et al., "Synthesis of Aminosalicylate–based polyanhydride Prodrugs: Esters, Amides, and Azos", *American Chemical Society, Abstracts of Papers, Part 2, Abstract No. 407,* 222nd ACS National Meeting, Chicago, IL, 1 p., (Aug. 2001).

Yazdi, M., et al., "Effects of non–steroidal anti–inflammatory drugs on demineralized bone–induced bone formation", *Journal of Periodontal Research, 27* (1), pp. 28–33, (Jan. 1992).

* cited by examiner

POLYANHYDRIDE LINKERS FOR PRODUCTION OF DRUG POLYMERS AND DRUG POLYMER COMPOSITIONS PRODUCED THEREBY

RELATED APPLICATION

This application is a continuation-in-part of U.S. patent application Ser. No. 09/422,294, filed Oct. 21, 1999, which is a continuation-in-part of International Application No. PCT/US98/18816, filed Sep. 10, 1998, which claims priority to U.S. Provisional Patent Application Serial No. 60/058,328, filed Sep. 10, 1997, all of which are incorporated herein by reference in their entirety.

FILED OF THE INVENTION

Biocompatibie polyanhydride linkers having improved degradation properties for use in the production of drug polymers have now been developed. These linkers serve as the polymeric backbone of degradable polymer drug delivery systems for a multitude of low molecular weight drugs which comprise within their structure one carboxylic acid group as well as at least one amine, thiol, alcohol or phenol group. Drug polymers linked via these biocompatible, biodegradable polyanhydrides can be administered to a host by a variety of routes including, but not limited to orally, subcutaneously, intramuscularly, intradermally and topically, depending upon the drug linked via the polyanhydride and the selected use for the drug.

BACKGROUND OF THE INVENTION

Polymers comprising aromatic or aliphatic anhydrides have been studied extensively over the years for a variety of uses. For example, in the 1930s fibers comprising aliphatic polyanhydrides were prepared for use in the textile industry. In the mid 1950s, aromatic polyanhydrides were prepared with improved film and fiber forming properties. More recently, attempts have been made to synthesize polyanhydrides with greater thermal and hydrolytic stability and sustained drug release properties.

U.S. Pat. Nos. 4,757,128 and 4,997,904 disclose the preparation of polyanhydrides with improved sustained drug release properties from pure, isolated prepolymers of diacids and acetic acid. However, these biocompatible and biodegradable aromatic polyanhydrides have radical or aliphatic bonds resulting in compounds with slow degradation times as well as relatively insoluble degradation products unless incorporated into a copolymer containing a more hydrophilic monomer, such as sebacic acid. The aromatic polyanhydrides disclosed in the '128 Patent and the '904 Patent are also insoluble in most organic solvents. A bioerodible controlled release device produced as a homogenous polymeric matrix from polyanhydrides with aliphatic bonds having weight average molecular weights greater than 20,000 and an intrinsic velocity greater than 0.3 dL/g and a biologically active substance is also described in U.S. Pat. No. 4,888,176. Another bioerodible matrix material for controlled delivery of bioactive compounds comprising polyanhydride polymers with a uniform distribution of aliphatic and aromatic residues is disclosed in U.S. Pat. No. 4,857,311.

Biocompatible and biodegradable aromatic polyanhydrides prepared from para-substituted bis-aromatic dicarboxylic acids for use in wound closure devices are disclosed in U.S. Pat. No. 5,264,540. However, these compounds exhibit high melt and glass transition temperatures and decreased solubility, thus making them difficult to process. The disclosed polyanhydrides also comprise radical or aliphatic bonds which can not be hydrolyzed by water.

Polyanhydride polymeric matrices have also been described for use in orthopedic and dental applications. For example, U.S. Pat. No. 4,886,870 discloses a bioerodible article useful for prosthesis and implantation which comprises a biocompatible, hydrophobic polyanhydride matrix. U.S. Pat. No. 5,902,599 also discloses biodegradable polymer networks for use in a variety of dental and orthopedic applications which are formed by polymerizing anhydride prepolymers.

Biocompatible and biodegradable polyanhydrides have now been developed with improved degradation, processing and solubility properties, as well as utilities based upon their degradation products.

SUMMARY OF THE INVENTION

An object of the present invention is to provide biocompatible and biodegradable polyanhydrides which serve as the polymeric backbone linking drug molecules into polymeric drug delivery systems. These polyanhydrides demonstrate enhanced solubility and processability, as well as degradation properties due to the use of hydrolyzable bonds such as esters, amides, urethanes, carbamates and carbonates as opposed to radical or aliphatic bonds. The polyanhydride linker of the present invention comprises the structure of Formula I:

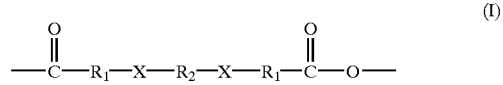

wherein $R_1$ is selected from the group consisting of alkyls, cycloalkyls, substituted alkyls, aromatics, substituted aromatics, lactams, and lactones; X is selected from the group consisting of amides, thioamides, esters and thioesters; and $R_2$ is an alkyl represented by $—(CH_2)_n$ wherein n is from 1 to 20.

This polyanhydride is used to link low molecular weight drug molecules comprising within their molecular structure one carboxylic acid group and at least one amine, thiol, alcohol or phenol group. Accordingly, polyanhydrides of Formula (I) serve as the polymer backbone of polymeric drug delivery systems comprising these low molecular weight drugs.

Thus, the present invention also relates to compositions, methods of producing compositions and methods of using compositions comprising a polyanhydride of Formula (I) and low molecular weight drug molecules containing within their structure one carboxylic acid group and at least one amine, thiol, alcohol or phenol group, wherein molecules of the drug are linked to one another via the polyanhydride. These polymeric drug delivery systems provide an effective means to deliver drugs in a controlled fashion to any site of a host. By "host" it is meant to include both animals and plants.

A more complete appreciation of the invention and other intended advantages can be readily obtained by reference to the following detailed description of the preferred embodiments and claims, which disclose the principles of the invention and the best modes which are presently contemplated for carrying them out.

DETAILED DESCRIPTION OF THE INVENTION

Biodegradable, biocompatible polyanhydrides which serve as linkers for low molecular weight drug molecules have now been developed. Compositions comprising low molecular weight drugs linked via polyanhydrides of the present invention are useful in a variety of applications wherein delivery of the drugs in a controlled fashion is desired. For purposes of the present invention, by "low molecular weight drug" it is meant to include any compound with one carboxylic acid group and at least one amine, thiol, alcohol or phenol group within its structure, wherein the compound has a demonstrated pharmacological activity and a molecular weight of approximately 1000 daltons or less.

In the present invention, the polyanhydride comprises the structure of Formula I:

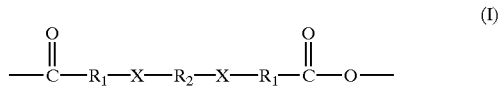

(I)

wherein $R_1$ is selected from the group consisting of alkyls, cycloalkyls, substituted alkyls, aromatics, substituted aromatics, lactams, and lactones; X is selected from the group consisting of amides, thioamides, esters and thioesters; and $R_2$ is an alkyl represented by —(CH2)$_n$, wherein n is from 1 to 20.

In one embodiment, polyanhydrides of the present invention are prepared by the method described in Conix, Macromol. Synth., 2, 95–99 (1996). In this method, dicarboxylic acids are acetylated in an excess of acetic anhydride at reflux temperatures followed by melt condensation of the resulting carboxylic acid anhydride at 180° C. for 2–3 hours. The resulting polymers are isolated by precipitation into diethylether from methylene chloride. The described process is essentially the conventional method for polymerizing bisaromatic dicarboxylic acid anhydrides into aromatic polyanhydrides.

Polyanhydrides of the present invention have average molecular weights ranging between about 1500 daltons up to about 100,000 daltons, calculated by Gel Permeation Chromatography (GPC) relative to narrow molecular weight polystyrene standards.

It has been found that these polyanhydrides can serve as a polymer backbone for degradable polymeric drug delivery systems for a multitude of low molecular weight drugs. Drugs which can be linked into degradable copolymers via the polyanhydrides have the following characteristics. The drug must have a relatively low molecular weight of approximately 1,000 daltons or less. The drug must contain within its molecular structure one carboxylic acid group. In addition, the drug must contain at least one amine, thiol, alcohol or phenol group within its structure. Examples of such low molecular weight drugs with these functional groups within their structure can be found in almost all classes of drugs including, but not limited to, analgesics, anesthetics, antiacne agents, antibiotics, synthetic antibacterial agents, anticholinergics, anticoagulants, antidyskinetics, antifibrotics, antifungal agents, antiglaucoma agents, antiinflammatory agents, antineoplastics, antiosteoporotics, antipagetics, anti-Parkinson's agents, antipsoratics, antipyretics, antiseptics/disinfectants, antithrombotics, bone resorption inhibitors, calcium regulators, keratolytics, sclerosing agents and ultraviolet screening agents. Linkage of low molecular weight drugs meeting the structural requirements of a single carboxylic acid group and at least one amine, thiol, alcohol or phenol group within its structure are exemplified in the following Schemes 1 and 2.

Scheme 1 shows the linkage of amoxicillin in a polyanhydride of the present invention. As shown in the following scheme, the carboxylic acid group of the low molecular weight drug molecule is first protected, preferably via acetylation. The protected drug molecules are then exposed to a chlorinated form of the linker of Formula (I), referred to herein as Formula (II),

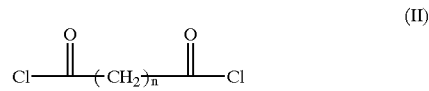

(II)

wherein n is from 1 to 20, so that the drug molecules displace the chlorine groups of Formula (II) and bind to the linker via the amine, thiol, alcohol or phenol groups of the drug molecules. The drug and linker are then exposed to heat and/or vacuum to remove the protecting groups, thereby resulting in a polymeric drug delivery system.

Scheme 1: Synthesis of Amoxicillin Polymer

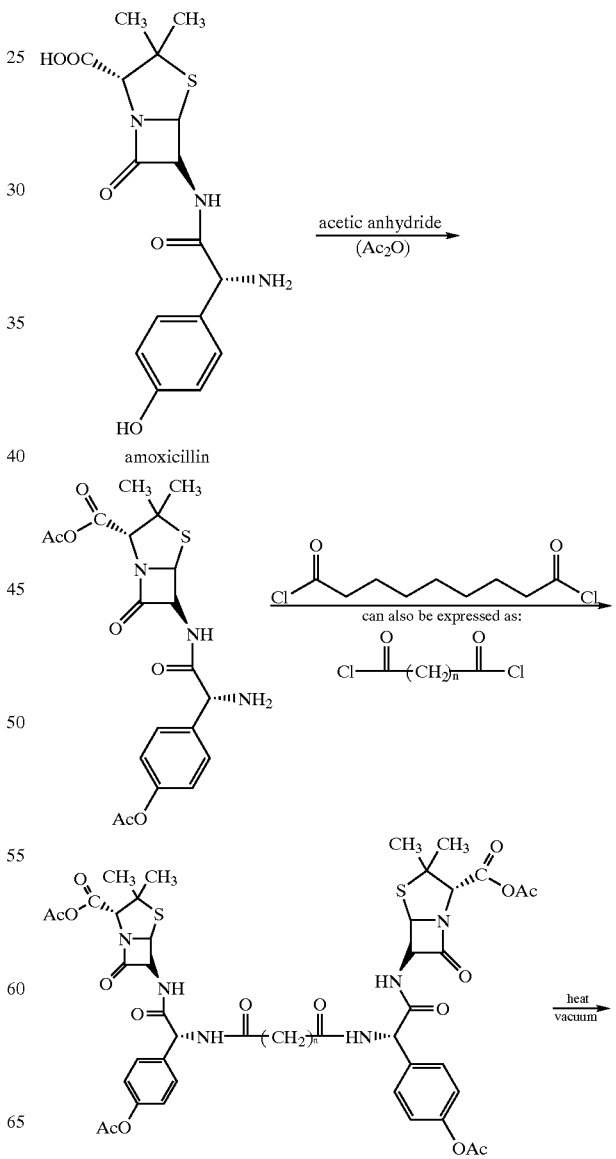

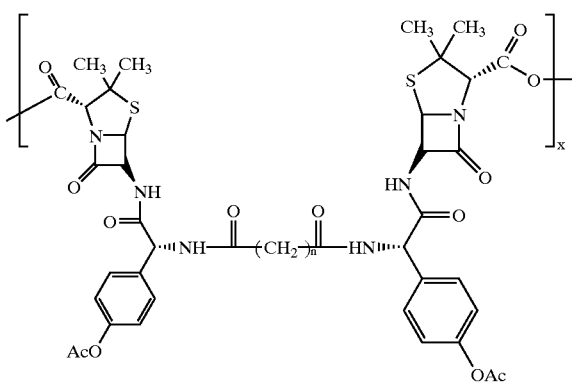

Scheme 2 shows the preparation of a cephalexin polymer. As depicted in this Scheme, the carboxylic acid of cephalexin is first protected, for example with a benzylic group. The drug is then linked to sebacyl chloride. Following this linkage, the protecting groups are removed to produce carboxylic acids which are then acetylated to produce monomer. The monomer is polymerized as a melt.

Scheme 2: Sythesis of Cephalexin Polymer

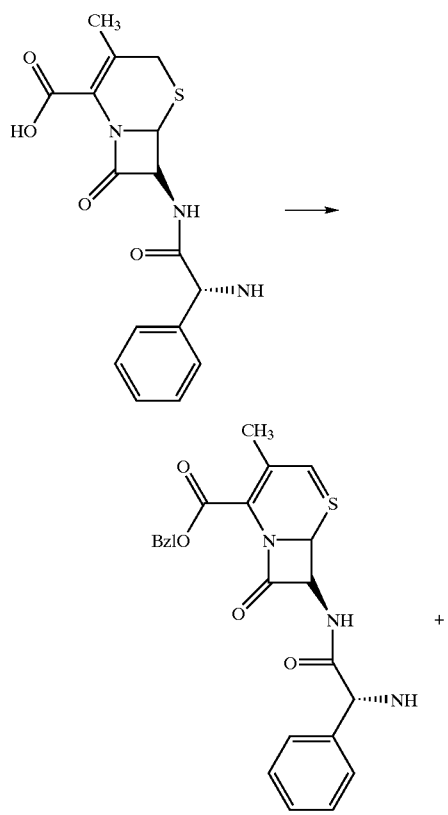

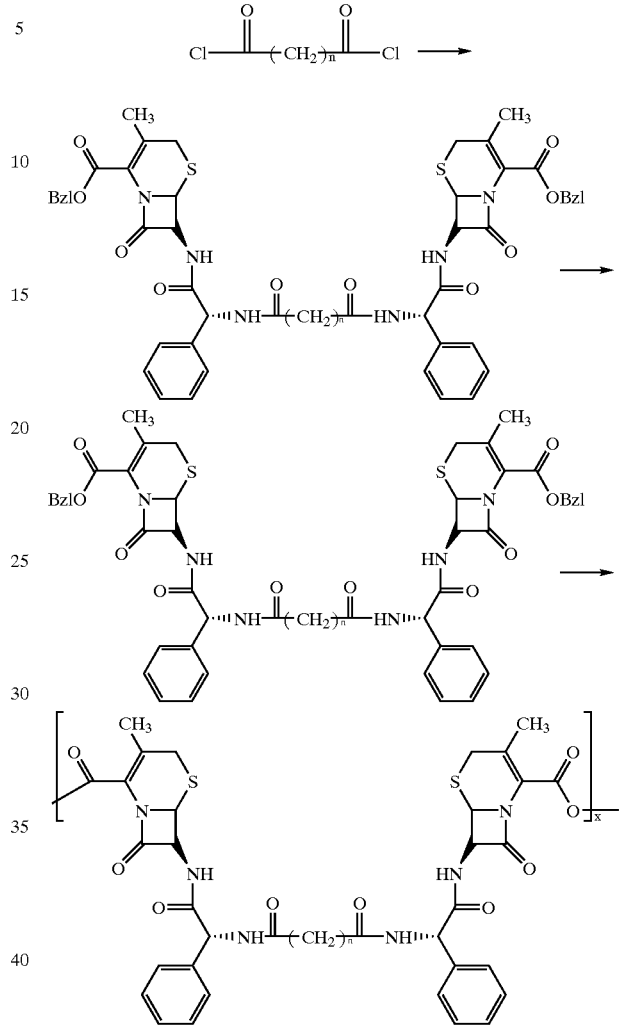

Examples of other polymeric drug delivery systems which can be prepared in accordance with this method via the polyanhydride linker of Formula (I) of the present invention include, but are certainly not limited to, a carbidopa delivery system, a levodopa delivery system and an amtenac delivery system. Homopolymers of the carbidopa and levodopa drug delivery systems are depicted in Formulas (III) and (IV), respectively.

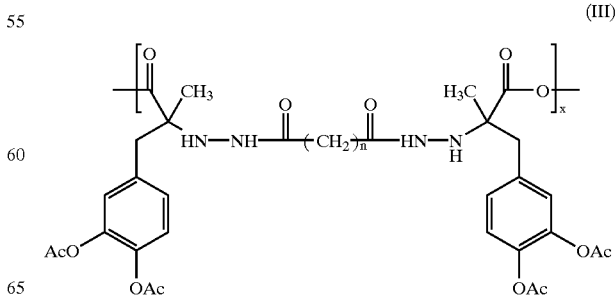

(III)

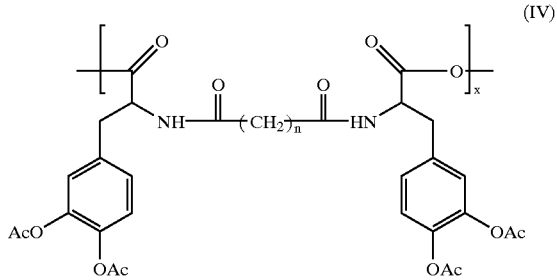

(IV)

While these structures depict homopolymers, copolymers of such drugs can also be prepared routinely based upon the teachings provided herein. Further, polymeric drug delivery systems comprising the polyanhydride of Formula (I) and other drugs meeting the structural requirements, namely one carboxylic acid group, at least one amine, thiol, alcohol or phenol group, and having a molecular weight of approximately 1000 daltons or less can also be routinely prepared via the disclosed methods.

Polyanhydride linkers of the present invention can be isolated by known methods commonly employed in the field of synthetic polymers and used to produce a variety of drug delivery products with valuable physical and chemical properties. Polymeric drug delivery systems comprising this polyanhydride linker can be readily processed into pastes or solvent cast to yield films, coatings, microspheres and fibers with different geometric shapes for design of various medical implants, and may also be processed by compression molding and extrusion. Medical implant applications include the use of polyanhydrides to form shaped articles such as vascular grafts and stents, bone plates, sutures, implantable sensors, implantable drug delivery devices, stents for tissue regeneration, and other articles that decompose harmlessly while delivering a selected low molecular weight drug at the site of implantation within a known time period. Drugs linked via these polyanhydrides of the present invention can also be incorporated into oral formulations and into products such as skin moisturizers, cleansers, pads, plasters, lotions, creams, gels, ointments, solutions, shampoos, tanning products and lipsticks for topical application.

The quantity of polymeric drug to be administered to a host which is effective for the selected use can be readily determined by those of ordinary skill in the art without undue experimentation. The quantity essentially corresponds stoichiometrically to the amount of drug which is known to produce an effective treatment for the selected use.

The present invention also relates to methods of using compositions comprising these low molecular weight drugs linked via the polyanhydrides in any application wherein delivery of the low molecular weight drug is desired. Route of delivery is selected in accordance with drug being administered and the condition being treated. For example, compositions of the present invention comprising a polyanhydride of Formula (I) linking a low molecular weight drug such as amoxicillin or cephalexin can be administered orally or topically to treat bacterial infections. Similarly, compositions of the present invention comprising a polyanhydride of Formula (I) linking a low molecular weight drug such as carbidopa or levodopa can be administered orally to patients suffering from Parkinson's disease to alleviate the symptoms of this disease.

In one embodiment of the present invention, the polyanhydride of Formula (I) is used to link two different low molecular weight drugs into a single polymeric drug delivery system. For example, the polyanhydride of Formula (I) can be used to link a drug molecule of carbidopa with a drug molecule of levodopa so that both drugs can be delivered simultaneously via a single polymeric drug delivery system.

Characteristics of the compositions of the present invention can be determined by a proton nuclear magnetic resonance (NMR) spectroscopy, infrared (IR) spectroscopy, gel permeation chromatography (GPC), high performance liquid chromatography (HPLC), differential scanning calorimetry (DSC), and thermal gravimetric analysis (TGA). Infrared spectroscopy is performed on samples prepared by solvent casting on NaCl plates. $^1$H and $^{13}$C NMR spectroscopy is obtained on in solutions of $CDCl_3$ or $DMSO-d_6$ with solvent as the internal reference. GPC is performed to determine molecular weight and polydispersity on samples dissolved in tetrahydrofuran and eluted through a mixed bed column (PE PL gel, 5 μm mixed bed) at a flow rate of 0.5 mL/minute. Samples (about 5 mg/mL) are dissolved into the tetrahydrofuran and filtered using 0.5 μm PTFE syringe filters prior to column injection. Molecular weights are determined relative to narrow molecular weight polystyrene standards (Polysciences, Inc.). Thermal analysis is performed for example on a Perkin-Elmer system consisting of a TGA 7 thermal gravimetric analyzer equipped with PE AD-4 autobalance and Pyris 1 DSC analyzer. Pyris software is used to carry out data analysis on a DEC Venturis 5100 computer. For DSC, an average sample weight of 5–10 mg is heated at 10° C./minute at a 30 psi flow of $N_2$. For TGA, an average sample weight of 10 mg is heated at 20° C./minute under a 8 psi flow of $N_2$. Sessile drop contact angle measurements are obtained with an NRL Goniometer (Rame-hart) using distilled water. Solutions of polymer in methylene chloride (10% wt/volume) are spun-coated onto glass slips, at 5,000 rpm for 30 seconds.

What is claimed is:

1. A polyanhydride comprising repeating units of Formula (1):

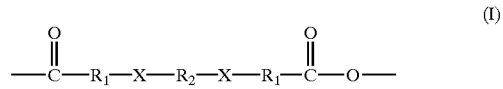

(I)

wherein

R$_1$ is a low molecular weight drug molecule comprising a carboxylic acid group and at least one amine, thiol, alcohol or phenol group;

X is selected from the group consisting of amides, thioamides, esters and thioesters; and R$_2$ is an alkyl represented by —(CH$_2$)$_n$, wherein n is from 1 to 20.

2. A method of delivering a low molecular weight drug to a patient comprising administering to the patient a polyanhydride of claim 1.

3. The polyanhydride of claim 1, wherein the low molecular weight drug is amoxycillin, cephalexin, carbidopa or levodopa.

\* \* \* \* \*

UNITED STATES PATENT AND TRADEMARK OFFICE
CERTIFICATE OF CORRECTION

PATENT NO. : 6,486,214 B1  Page 1 of 1
DATED : November 26, 2002
INVENTOR(S) : Kathryn E. Uhrich Ph.D.

It is certified that error appears in the above-identified patent and that said Letters Patent is hereby corrected as shown below:

<u>Title page,</u>
Item [56], OTHER PUBLICATIONS, 2nd "Attawia, M.A., et al.", reference, delete "Cytototoxicity" and insert -- Cytotoxicity -- therefor.

<u>Column 8,</u>
Line 41, delete "(1)" and insert -- (I) -- therefor.

Signed and Sealed this

Ninth Day of September, 2003

JAMES E. ROGAN
*Director of the United States Patent and Trademark Office*